(12) United States Patent
Caucci et al.

(10) Patent No.: US 12,718,374 B2
(45) Date of Patent: Aug. 25, 2026

(54) DATA ACQUISITION AND MEASUREMENT OF CHARACTERISTIC FUNCTIONALS IN BIOLOGY AND MEDICINE

(71) Applicant: Arizona Board of Regents on Behalf of the University of Arizona, Tucson, AZ (US)

(72) Inventors: Luca Caucci, Tucson, AZ (US); Harrison H. Barrett, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 657 days.

(21) Appl. No.: 18/249,940

(22) PCT Filed: Oct. 22, 2021

(86) PCT No.: PCT/US2021/056205
§ 371 (c)(1),
(2) Date: Apr. 20, 2023

(87) PCT Pub. No.: WO2022/087378
PCT Pub. Date: Apr. 28, 2022

(65) Prior Publication Data

US 2023/0386039 A1 Nov. 30, 2023

Related U.S. Application Data

(60) Provisional application No. 63/105,036, filed on Oct. 23, 2020.

(51) Int. Cl.

| | |
|---|---|
| ***G01N 21/64*** | (2006.01) |
| ***G06T 7/00*** | (2017.01) |
| ***G16H 50/50*** | (2018.01) |

(52) U.S. Cl.
CPC .......... *G06T 7/0016* (2013.01); *G16H 50/50* (2018.01); *G06T 2207/10056* (2013.01);
(Continued)

(58) Field of Classification Search
CPC ......... G06T 7/0016; G06T 2207/10056; G06T 2207/10064; G06T 2207/10104;
(Continued)

(56) References Cited

U.S. PATENT DOCUMENTS

| | | |
|---|---|---|
| 5,590,215 A | 12/1996 | Allen |
| 2009/0306520 A1 | 12/2009 | Schmitt et al. |

(Continued)

FOREIGN PATENT DOCUMENTS

| | | | |
|---|---|---|---|
| WO | WO 2013/106760 | 7/2013 | |
| WO | WO-2013106760 A1 * | 7/2013 | ......... G01N 21/4795 |

OTHER PUBLICATIONS

Minamimoto R, Hotta M, Ishikane M, Inagaki T. FDG-PET/CT images of COVID-19: a comprehensive review. Global Health & Medicine. Aug. 31, 2020;2(4):221-6. (Year: 2020).*

(Continued)

*Primary Examiner* — Gregory A Morse
*Assistant Examiner* — Renae A Bitor
(74) *Attorney, Agent, or Firm* — LEYDIG, VOIT & MAYER, LTD.

(57) ABSTRACT

Many biologic processes taking place inside a living organism are unpredictable in time and space, and cannot be known exactly. These mechanisms and interactions among them are better modeled as physiological random processes, the statistics of which are fully described by joint characteristic functionals. The present invention provides methods for the estimation of joint characteristic functionals through imaging of multiple physiological random processes. This technology can be used to study complex diseases, such as (Continued)

tumors and viral infections, by imaging the biological processes involved with disease progression and response to treatment.

21 Claims, 4 Drawing Sheets

(52) U.S. Cl.
CPC ............... *G06T 2207/10064* (2013.01); *G06T 2207/10104* (2013.01); *G06T 2207/10108* (2013.01); *G06T 2207/30024* (2013.01)

(58) Field of Classification Search
CPC . G06T 2207/10108; G06T 2207/30024; G06T 7/0012; G06T 2207/20076; G06T 2207/30096; G16H 50/50; G16H 30/20; G16H 30/40; G16H 50/80; G16H 50/30; A61B 5/0071; A61B 5/0033; A61B 5/0077; A61B 2576/00; A61B 6/037; G01N 21/6458; G01N 2021/6439; G16B 20/00
See application file for complete search history.

(56) References Cited

U.S. PATENT DOCUMENTS

2013/0315491 A1* 11/2013 Konofagou .......... A61B 8/5207 382/209
2014/0153795 A1* 6/2014 Lenox .................. G06T 7/0012 382/128
2018/0271473 A1* 9/2018 Carmi .................... A61B 6/582

OTHER PUBLICATIONS

Auclair et al. (2007) "Bone morphogenetic protein signaling is essential for terminal differentiation of the intestinal secretory cell lineage," Gastroenterology, 133(3), p. 887-96, PMID: 17678919, DOI: 10.1053/j.gastro.2007.06.066.
Barrett (Jan./Feb. 2020) "Is there a role for image science in the brave new world of artificial intelligence?" Journal of Medical Imaging 7, 012702.
Barrett et al. (2004) "8.2.3 Characteristic functionals," Foundations of Image Science, Wiley-Interscience, Hoboken, NJ.
Barrett et al. (2016) "Therapy operating characteristic curves: tools for precision chemotherapy," Journal of Medical Imaging 3, 023502.
Barrett et al. (Dec. 2020) "Stochastic models for objects and images in oncology and virology: Application to PI3K-Akt-mTOR signaling and COVID-19 disease," Journal of Medical Imaging, vol. 8, Issue S1, S16001.
Belouzard et al. (2012) "Mechanisms of coronavirus cell entry mediated by the viral spike protein," Viruses 4, 1011-1033.
Bhattacharyya (1943) "On a measure of divergence between two statistical populations defined by their probability distributions," Bulletin of the Calcutta Mathematical Society, 35, p. 99-109.
Blanpain et al. (2014) "Stem cell plasticity. Plasticity of epithelial stem cells in tissue regeneration," Science, 344(6189), p. 1242281, PMID: 24926024, PMCID: PMC4523269, DOI: 10.1126/science.1242281.
Burvall et al. (2006) "Singular-value decomposition for through-focus imaging systems," Journal of the Optical Society of America. A, Optics, image science, and vision, 23(10), p. 2440-8, PMID: 16985529, DOI: 10.1364/josaa.23.002440.
Burvall et al. (2010) "Singular-value decomposition of a tomosynthesis system," Optics express, 18(20), p. 20699-711, PMID: 20940966, PMCID: PMC2958053, DOI: 10.1364/OE.18.020699.
Callaway (Sep. 2020) "Making Sense of Coronavirus Mutations," Nature 585, 174-177.
Chen et al. (2009) "Small molecule-mediated disruption of Wnt-dependent signaling in tissue regeneration and cancer," Nature chemical biology, 5(2), p. 100-7, PMID: 19125156, PMCID: PMC2628455, DOI: 10.1038/nchembio.137.
Clarkson et al. (2016) "Characteristic functionals in imaging and image-quality assessment: tutorial," Journal of the Optical Society of America A, vol. 33, No. 8, 1464.
Cuny et al. (2008) "Structure-activity relationship study of bone morphogenetic protein (BMP) signaling inhibitors," Bioorganic & medicinal chemistry letters, 18(15), p. 4388-92, PMID: 18621530, PMCID: PMC2570262, DOI: 10.1016/j.bmcl.2008.06.052.
Ding et al. (2017) "Charged-particle emission tomography," Medical Physics 44, 2478-2489.
Eskin et al. (1994) "Recovery of spectral information from an imperfect detector using the expectation maximization algorithm," in Proceedings of 1994 IEEE Nuclear Science Symposium, 150-154.
Flanagan et al. (2018) "Wnt Signalling in Gastrointestinal Epithelial Stem Cells," Genes, 9(4), PMID: 29570681, PMCID: PMC5924520, DOI: 10.3390/genes9040178.
Gao et al. (2011) "PI3K/Akt signaling requires spatial compartmentalization in plasma membrane microdomains," Proceedings of the National Academy of Sciences of the United States of America 108, 14509-14514.
He et al. (2004) "BMP signaling inhibits intestinal stem cell self-renewal through suppression of Wnt-β-catenin signaling," Nature genetics, 36(10), p. 1117-21, PMID: 15378062, DOI: 10.1038/ng1430.
Henscheid et al. (2018) "Physiological random processes in precision cancer therapy," PLoS One 13(6): e0199823. https://doi.org/10.1371/journal.pone.0199823.
Hofer et al. (Feb. 2021) "Engineering organoids," Nature reviews. Materials, p. 1-19, PMID: 33623712, PMCID: PMC7893133, DOI: 10.1038/s41578-021-00279-y.
International Search Report and Written Opinion, dated Jan. 25, 2022, corresponding to International Application No. PCT/US2021/056205, (from which the present application claims priority,) 11 pp.
Kim et al. (Jul. 2020) "Human organoids: model systems for human biology and medicine," Nature reviews. Molecular cell biology, 21(10), p. 571-584, PMID: 32636524, PMCID: PMC7339799, DOI: 10.1038/s41580-020-0259-3.
Korber et al. (Aug. 2020) "Tracking Changes in SARS-CoV-2 Spike: Evidence that D614G Increases Infectivity of the COVID-19 Virus," Cell 182, 812-827.
Li et al. (Mar. 2020) "Early transmission dynamics in Wuhan, China, of novel coronavirus-infected pneumonia," The New England Journal of Medicine 382, 1199-1207.
Maloy et al. (2011) "Intestinal homeostasis and its breakdown in inflammatory bowel disease," Nature, 474(7351), p. 298-306, PMID: 21677746, DOI: 10.1038/nature10208.
Markevich et al. (2006) "Long-range signaling by phosphoprotein waves arising from bistability in protein kinase cascades," Molecular Systems Biology 2, 61.
Nile et al. (Jun. 2020) "COVID-19: Pathogenesis, cytokine storm and therapeutic potential of interferons," Cytokine and Growth Factor Reviews 53, 66-70.
Radtke et al. (2005) "Self-renewal and cancer of the gut: two sides of a coin," Science (New York, N.Y.), 307(5717), p. 1904-9, PMID: 15790842, DOI: 10.1126/science.1104815.
Schepers et al. (2012) "Wnt signaling, stem cells, and cancer of the gastrointestinal tract," Cold Spring Harbor perspectives in biology, 4(4), p. a007989, PMID: 22474007, PMCID: PMC3312683, DOI: 10.1101/cshperspect.a007989.
Sulaimanov et al. (2017) "Understanding the mTOR signaling pathway via mathematical modeling," Wiley Interdisciplinary Reviews: Systems Biology and Medicine 9(4), e1379.
Terzić et al. (2010) "Inflammation and colon cancer," Gastroenterology, 138(6), p. 2101-2114.e5, PMID: 20420949, DOI: 10.1053/j.gastro.2010.01.058.
Thorne et al. (2018) "Enteroid Monolayers Reveal an Autonomous WNT and BMP Circuit Controlling Intestinal Epithelial Growth and Organization," Developmental Cell 44(5), 624-633.

(56) References Cited

OTHER PUBLICATIONS

Timmer (Mar. 2020) "COVID-19: The biology of an effective therapy," Ars Technica.
Wang et al. (Feb. 2020) "A novel coronavirus outbreak of global health concern," The Lancet 395, 470-473.
Wang et al. (May 2020) "The role of high cholesterol in age-related COVID19 lethality," bioRxiv 2020.05.09.086249; doi: https://doi.org/10.1101/2020.05.09.086249.
Wu et al. (Feb. 2020) "A new coronavirus associated with human respiratory disease in China," Nature 579, 265-269.

* cited by examiner

DATA ACQUISITION AND MEASUREMENT OF CHARACTERISTIC FUNCTIONALS IN BIOLOGY AND MEDICINE

CROSS-REFERENCE TO RELATED APPLICATIONS

This application is a U.S. National Stage Application filed under 35 U.S.C. § 371 of International Application No. PCT/US2021/056205, filed Oct. 22, 2021, which claims the benefit of priority to U.S. Provisional Patent Application No. 63/105,036, filed Oct. 23, 2020, both of which are specifically incorporated by reference to the extent not inconsistent herewith.

STATEMENT REGARDING FEDERALLY SPONSORED RESEARCH OR DEVELOPMENT

This invention was made with government support under Grant No. R01 EB000803 and P41 EB002035 awarded by NIH. The government has certain rights in the invention.

BACKGROUND OF THE INVENTION

Physiology is the study of life. It includes the study of complex interactions often involving proteins, enzymes, body fluids, selective membranes, therapeutic agents, etc. Given the complexity of these interactions, most biological researchers concentrate on a subset of these effects, which are referred to as a physiological process. This invention introduces new and powerful methods of imaging physiological processes.

In clinical medicine, the most common current methods of imaging physiological processes in humans are PET (Positron Emission Tomography) and SPECT (Single-Photon Emission Computed Tomography). Both of these modalities use radioactive isotopes that either have a natural affinity for the physiological process of interest or that are linked to a nonradioactive molecule, called a "tracer", that supplies the affinity. The nuclear decay processes can be complicated, but in both PET and SPECT the end result is one or more gamma rays per nuclear decay event. These data can be used with well-known algorithms to reconstruct images of physiological objects.

Though the methods outlined in paragraph above are ubiquitous in clinical medicine, they fall far short of providing a comprehensive picture of the physiology of interest. Physiology in living subjects is inherently dynamic, so fine details of the tracer distribution are essentially invisible.

Moreover, many biologic processes taking place inside a living organism are unpredictable with regard to time and space and cannot be exactly known. These biological processes usually cannot be adequately characterized using typical imaging methods. The mechanisms and interactions among these biological processes are better modeled as random physiological processes, the statistics of which can be described by joint characteristic functionals.

A characteristic functional is a mathematical construct used to quantify statistical properties of random fields and generalized random fields (see, for example, Clarkson and Barrett, Journal of the Optical Society of America A 33, 1464-1475 (2016)). More specifically, a characteristic functional completely defines the probability distribution of a random field (see also Barrett and Myers, "Foundations of Image Science," Wiley-Interscience, Hoboken, NJ (2004); and Henscheid et al., PloS One 13 (6), e0199823 (2018)).

In the case of an imaging system, one might be interested in the statistical properties of the image data and those of the object that produced them. If the multivariate probability density function (PDF) for image data is known, then the characteristic function for the images can be calculated, such as through a Fourier transformation of the PDF. For objects, which are functions of continuous variables rather than discrete pixels or voxels, the characteristic function becomes infinite-dimensional, and it is referred to as the characteristic functional.

There are many cases in which the mathematical form of a characteristic functional can be known analytically from first principles, thereby allowing the estimable properties of the object to be estimated. Moreover, if the characteristic functional for the object is known, the corresponding characteristic function for the image data can also be readily computed. Accordingly, in order to better analyze and generate models of biological and physiological processes, especially in vivo, what is needed are methods and systems able to estimate the characteristic functionals of the biological and physiological processes.

SUMMARY OF THE INVENTION

The present invention provides methods for determining and estimating joint characteristic functionals of biological and physiological processes in tissue using imaging. In one aspect, the present invention enables the study of complex diseases, such as tumors and viral infections, by imaging the biological processes involved with disease progression and responses to treatment, and then analyzing the characteristic functionals obtained from these images.

In an embodiment, the present invention provides a method for analyzing a cell or tissue comprising the steps of: a) performing multiple imaging scans of one or more cells or tissues containing a selected molecule or structure of interest; b) generating image data of one or more physical characteristics of the molecule or structure of interest from the imaging scans; c) calculating or estimating a characteristic functional for the one or more physical characteristics based on the image data; and d) analyzing the characteristic functional to generate modeling data or extract information from the selected molecule or structure of interest.

As used herein, the molecules or structures may be any molecule or structure that is part of a biological pathway, including those affected by diseases. Suitable molecules include but are limited to antibodies, polypeptides, proteins, cell receptors, and nucleic acids. Suitable structures include but are not limited to biological structures such as tumors, lymph nodes, tissue growths, cells, and cellular components.

The image data is used to generate a characteristic functional for one or more physical characteristics of the molecule or structure of interest. Such physical characteristics as used in the embodiments described herein include but are not limited to: i) presence of the molecule or structure in one or more cells or tissues; ii) quantity of the molecule or structure in one or more cells or tissues; iii) location of the molecule or structure within the one or more cells or tissues; iv) binding of the molecules or structure to a second molecule; v) conformational structure of the molecule or structure of interest; vi) size of the structure of interest; or vii) combinations thereof.

Optionally, the data generated from the characteristic functional is used to determine an increase or decrease in the amount of the molecules or structures of interest, interactions of the molecules or structures of interest with other molecules or structures, or conformational changes of the molecules or structures of interest over time or in response to exposure to a chemical, biomolecule or drug. For example, the present invention is used to indicate whether the interaction or physical structure of a particular molecule in a biological pathway is altered when the cell or tissue is exposed to a virus; or whether the size or shape of a particular biological structure is affected by administration of a chemical, biological agent or drug. In an embodiment, the data generated from the characteristic functional is used to determine the sensitivity of a molecule or structure to administration of a chemical, biological agent or drug, or to determine the proliferation, differentiation or migration of a molecule or biological structure during a biological process.

Preferably, imaging methods used herein comprise measuring radiation from multiple regions from the one or more cells or tissues, wherein the measured radiation is used to generate the image data. As used herein, "radiation" refers to visible and non-visible portions of the electromagnetic spectrum, including but not limited to infrared light, visible light, ultra violet light and combinations thereof. In an embodiment, the light is reflected or emitted from the cell or tissue being imaged, including but not limited to light emitted by a fluorescently labeled molecule. Alternatively, the image scans and data are obtained from positron emission tomography (PET) or single-photon emission computed tomography (SPECT).

In certain embodiments, this invention provides methods for the estimation of joint characteristic functionals by way of ultrafast imaging of multiple physiological random processes. For example, multiple physiological processes may be imaged using fluorescence imaging of tissue, where each process is labelled with a different fluorescent dye. In an embodiment, any fluorescent imaging system or camera as known in the art may be used. One exemplary embodiment uses a high-resolution camera to collect fluorescence light emitted by a thick tissue sample. When the tissue sample is axially translated, different planes in the tissue sample are in focus. In an alternative embodiment, light-sheet microscopy is used to illuminate a plurality of thin sections of a thick tissue sample.

In an embodiment, the present invention provides a method for analyzing a cell or tissue comprising the steps of: a) labeling a molecule or structure of interest with a fluorescent tag; b) irradiating one or more cells or tissues containing the labeled molecule or structure of interest with excitation radiation, thereby causing the labeled molecule or structure of interest to emit light; c) performing multiple imaging scans of the one or more cells or tissues containing the labeled molecule or structure of interest, wherein emitted light from multiple regions from the one or more cells or tissues is measured; d) generating image data of one or more physical characteristics of the labeled molecule or structure of interest from the measured radiation; e) calculating or estimating a characteristic functional for the one or more physical characteristics based on the image data; and f) analyzing the characteristic functional to generate modeling data for or extract information from the labeled molecule or structure of interest.

The excitation radiation may be any type of radiation able to cause a fluorophore to emit fluorescent light having a different wavelength than the excitation radiation. Preferably, the excitation radiation is ultra violet (UV) light. The emitted light may comprise visible light, non-visible light, or combinations thereof. The fluorescent tag may be any fluorescent tag or fluorescent dye as known in the art.

In an embodiment, the present invention provides a method for modeling a biological process in a cell or tissue comprising the steps of: a) performing multiple imaging scans of one or more cells or tissues containing a selected biological process of interest; b) generating image data of one or more physical characteristics related to the selected biological process; c) calculating or estimating a characteristic functional from said image data for the one or more physical characteristics; and d) analyzing the characteristic functional to generate modeling data for or extract information from the biological process. As described above, the physical characteristics related to the selected biological process include but are not limited to: i) presence of one or more molecules or structures in the cell or tissue; ii) quantity of one or more molecules or structures in the cell or tissue; iii) location of one or more molecules or structures within the cell or tissue; iv) binding of one or more molecules to a second molecule; v) conformational structure of one or more molecules; vi) size of one or more structures; or ii) combinations thereof.

Preferably, the biological process is related to a disease and the multiple scans are used to model progression of the disease. Optionally, the biological process is related to progression of a viral infection, preferably progression of COVID19 or infection of cells by a severe acute respiratory syndrome coronavirus. Alternatively, the biological process is related to a cancer or other disease related to mutations of mTOR signaling pathways or intestinal epithelium growth. Preferably, one or more imaging scans are performed prior to administering a treatment to the cell or tissue for the disease, and one or more imaging scans are performed after administering the treatment to the cell or tissue.

Optionally, multiple imaging scans of cells or tissues are taken from different patients so as to model the biological process across a population of patients. Alternatively, multiple imaging scans of cells or tissues are taken from the same patient so as to provide personalized and patient specific information. For example, multiple imaging scans of cells or tissues from the same patient are taken over time so as to analyzing a change in the one or more physical characteristics within that patient over time.

In a further embodiment, one or more proteins within the one or more cells or tissues are labelled with a fluorescent peptide prior to performing the multiple imaging scans. Image scans are obtained using a camera or imaging device able to transmit fluorescent excitation radiation to the one or more cells or tissues and measure resulting light emitted by a fluorescently labeled molecule. Alternatively, image scans are obtained from positron emission tomography (PET) or single-photon emission computed tomography (SPECT).

In an embodiment, the present invention determines an object characteristic functional and the corresponding characteristic function for images obtained from one or more biological applications, including but not limited to PI3K-Akt-mTOR signaling and COVID-19. These characteristic functionals and functions can then be used to visualize and model interactions associated with physiological processes, including potential treatments of a particular disease.

DETAILED DESCRIPTION OF THE INVENTION

Figure 1:
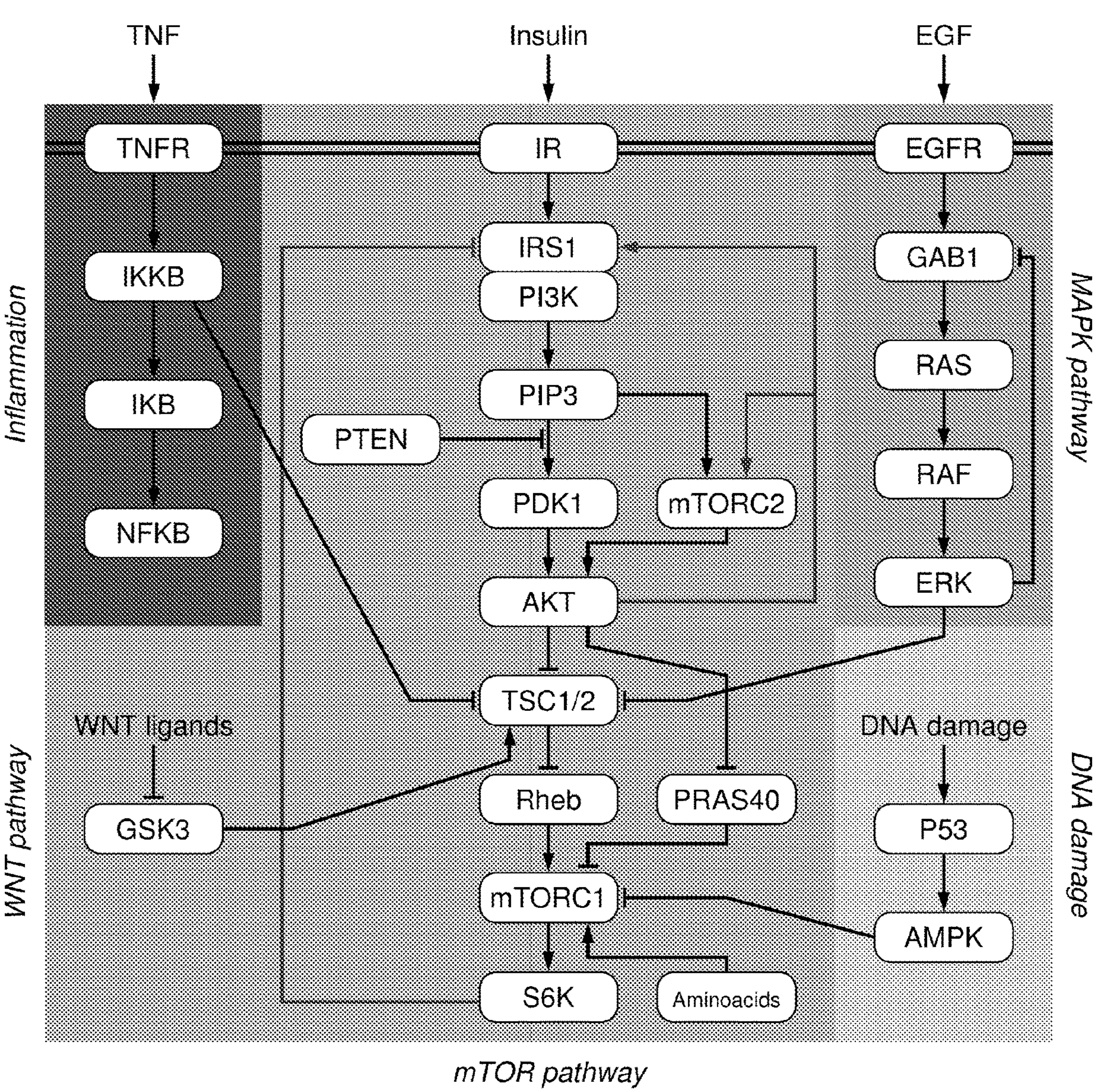
FIG. 1 shows a diagram of the mTOR pathway. The double line at the top of the diagram represents the plasma membrane, and the single light grey lines are feedback paths. Reproduced in modified form from Sulaimanov et al. (Wiley Interdisciplinary Reviews: Systems Biology and Medicine 9 (4), e1379 (2017)).

This invention is in the field of image acquisition and analysis and contributes to clinical patient management and scientific investigations for various diseases. Related mathematical underpinnings to methods described herein have been developed in journal papers and have been illustrated by simulation studies of various molecular imaging modalities, but there is a need for implementations that can be used with real patient data and real clinical objectives.

In examples described herein, embodiments of such implementations are illustrated by considering quite different disease types: cancers that involve mutations on the mTOR pathway, and coronoviral infections (specifically COVID-19). The former has the advantage that the biophysics of disease progression is well understood, while the latter will highlight some of the uncertainties in the biophysics and how they can be resolved.

In a further example, an embodiment is described that facilitates the study of two or more interacting physiological random processes in a thick tissue. The setup of FIG. 4 includes a UV light ring for the illumination of fluorescence fluorophores. Axial translations of the tissue sample will result in different planes being in focus; singular-value decomposition of a system of this kind shows that if a large number of high-resolution 2D frames are collected at different axial positions, depth information is recovered and 3D reconstruction is possible (see Surveil et al., Journal of the Optical Society of America. A, Optics, image science, and vision, 23 (10), 2440-8 (2006); and Burvall et al., Optics express, 18 (20), 20699-711 (2010)).

Throughout these examples it is assumed that the object being imaged is also the source of the radiation that forms the image. It is also assumed that the imaging systems are tomographic, meaning that they acquire information about the 3D structure of the object. Thus, these embodiments are in the realm of Emission Computed Tomography (ECT), which includes PET, SPECT, various form of optical fluorescent imaging, and the new modalities of Charged-Particle Emission Computed Tomography (CPET) for alpha and beta particles (Ding et al., Medical Physics 44, 2478-2489 (2017)). The specific embodiments described below do not consider CT, MRI or indirect optical methods such as fluorescence lifetime imaging.

The main mathematical tools to be utilized are characteristic functionals and characteristic functions, defined further in the next section. These tools lead to rigorous mathematical and statistical descriptions for physiological objects and their molecular images.

EXAMPLES

Example 1—Statistical Concepts and Notation

Digital images. A digital image, virtually by definition, is a finite set of numbers; were this not the case, the image could not be stored and processed in a computer or displayed on a monitor. In tomographic imaging it is common to associate a volume element (voxel) with every point in the digital image. In mathematical terms, the digital image is a vector in an M-dimensional vector space, where M is the number of voxels available to describe the image. Equivalently, the image can be treated as an (M×1) column vector, denoted g. The characteristic function of g can be defined as:

$$\psi_g(\xi) = \langle \exp(-2\pi i \xi^\dagger g) \rangle, \tag{1}$$

where the angle brackets denote a statistical average, and the superscript † denotes an adjoint (complex-conjugate transpose); thus $\xi^\dagger$ is a 1×M row vector, so $\xi^\dagger g$ is a scalar product. Note that $\psi_g(\xi)$ is a scalar, but it depends on the vector ξ, which can be chosen at will.

A simple interpretation of $\psi_g(\xi)$ is that it is the M-dimensional Fourier transform of the probability density function of the M-dimensional random vector g.

Objects: Physiological random processes. Physiology is the study of life. Thus molecular imaging of living cells and organisms should provide information about physiological processes. Moreover, very little about the biology of life is predictable. Etymologically, the opposite of predictable is stochastic, or random, so the objects being imaged in living organisms are physiological random processes (PRPs). Objects are functions of continuous variables, and images are sets of numbers. Technically, objects are vectors in an infinite-dimensional Hilbert space, and images are vectors in a finite-dimensional Euclidean space.

The simplest form of characteristic functional of a PRP is (cf. Eq.(1))

$$\Psi_f(\Phi) = \langle \exp[-2\pi i(\Phi, f)] \rangle, \tag{2}$$

where $f$ is a shorthand for a function of three spatial variables, $f=f(\boldsymbol{r})$, and $\boldsymbol{r}$=(x,y,z) (see H. H. Barrett, Journal of Medical Imaging 7, 012702 (2019)). Likewise, Φ is also a function of three spatial variables, hence a function in the same vector space as $f$, and the scalar product is defined as $$(\Phi, f) = \int_V d^3\, \mathrm{r}\ \Phi^*(\mathrm{r}) f(\mathrm{r}), \tag{3}$$

where V is the volume of integration, asterisk denotes complex conjugate, and $d^3\boldsymbol{r}$=dx dy dz.

From objects to images. It is often very easy to compute the characteristic function for an image if the characteristic functional of the object is known. As an example, consider a continuous-to-discrete (CD) linear operator $\mathcal{H}$. In the absence of excess detector noise, the imaging equation is $g=\mathcal{H}f$. If $\xi=\mathcal{H}\Phi$ in Eq. (1), the resulting equation is:

$$\psi_g(\xi)=\Psi_f(\mathcal{H}^\dagger\xi), \tag{4}$$

Thus, a simple change of variables in the argument converts $\Psi_f$ to $\psi_g$, thereby converting a characteristic functional to a characteristic function. The operator $\mathcal{H}^\dagger$ is referred to as back-projection in the tomography literature.

Multiple PRPs. In many situations it is useful to consider simultaneous ECT imaging of multiple, interacting PRPs. Much of the current research in molecular imaging revolves around the search for imaging biomarkers, defined loosely as a way to make a physiological random process apparent in a medical image. Intuitively, multiple biomarkers will be better than one, and a group of biomarkers will be more valuable still if there is a convincing theory that ties them together (see, for example, Henscheid et al., PloS One 13 (6), e0199823 (2018)).

As an example of a biological system with multiple PRPs where the characteristic functional can be expressed fairly succinctly, consider the basic problem of chemotherapy (Henscheid et al., PloS One 13 (6), e0199823 (2018); and Barrett et al., Journal of Medical Imaging 3, 023502 (2016)). Here the drug is usually administered intravenously, and it is transported into the tumor vasculature where it encounters a dense and complicated network of capillaries. Many papers in the systems-biology literature attempt to construct models of the capillaries, but the outcomes are seldom realistic, and virtually never do they capture the intricacies of the vasculature for a particular patient.

Minimally, at least three PRPs are needed to describe the drug distribution in the context of chemotherapy: the concentration of drug in the capillaries as a function of space and time; the vascular permeability as a function of position in the tumor, and the process where a drug molecule emerges from a capillary, diffuses to a tumor cell and binds to it.

If we let $f_1$ represent the drug concentration, $f_2$ the vascular permeability and $f_3$ the drug diffusion in the interstitium, respectively, then the form of the characteristic functional is:

$$\Psi_F(\Phi)=\langle\langle\langle\exp\{-2\pi i[(\Phi_1,f_1)+(\Phi_2,f_2)+(\Phi_3,f_3)]\}\rangle_{f_1|f_2,f_3}\rangle_{f_2|f_3}\rangle_{f_3}, \tag{5}$$

where F is the concatenation of the three terms and the subscripts on the angle brackets denote conditional averages; for example, $\langle\ldots\rangle_{f_1|f_2,f_3}$ denotes an average over $f_1$ with $f_2$ and $f_3$ held constant. Note that the order of averaging follows the physical flow of the therapy drug. In other words, there is no feedback in Eq. 5. A pathway where feedback plays a critical role is described further below.

Systems biology. Systems biology is a popular field of current research that often appears as a submission category in scientific meetings or biology journals. The mathematical models customarily used in systems biology can be (a) sets of coupled ordinary differential equations (ODEs); (b) sets of coupled partial differential equations (PDEs); (c) Boolean operators as in computer science, or (d) combinations of these objects. A recent review article that illustrates some of these choices in the context of the mTOR pathway is by Sulaimanov et al. (Wiley Interdisciplinary Reviews: Systems Biology and Medicine 9 (4), e1379 (2017)).

If ordinary differential equations are used, the variable of interest is almost always time, and model approaches the realm of compartmental modeling. Use of both spatial and temporal variables, hence PDEs, is more realistic but requires vastly more unknown parameters.

One fairly obvious way to study PRPs in a laboratory or clinic is to use monoclonal antibodies designed to bind to particular biomolecules of interest. These antibodies can be used with either fluorescent labels and optical imaging or with radioactive labels and SPECT imaging.

Laboratory studies with real tracers and imaging systems produce far richer data than would be available from a systems-biology simulation, especially with multiple PRPs. A single simulation run requires choosing mathematical forms for each PRP as a function of space and/or time, and the whole process must be repeated many times with different assumed forms for each PRP in order to learn anything about uncertainties in the systems-biology results. From a single real measurement of the characteristic functional, on the other hand, one can compute all means and variances and any other desired statistical properties of the real tracer distributions.

Example 2—Signaling Pathways

Structure of an example pathway. The pathway of interest here is PI3K/Akt/mTOR, where mTOR stands for mechanistic (or mammalian) target of Rapamycin.

Rapamycin was isolated in 1972 from bacteria found on Rapa Nui (Easter Island). It was initially developed as an antifungal agent. Rapamycin was soon found to inhibit mTOR, which makes it a potent immunosuppressive and antiproliferative agent. It is used widely to prevent rejection in organ transplantation. Deregulation of its signaling pathways is associated with numerous diseases affecting large populations, including obesity, diabetes and cancer. The pathway considered here is now regarded as a nearly universal physiological regulator.

A rigorous mathematical model of the PI3K/Akt/mTOR signaling pathway would be invaluable in patient-specific therapy of many cancers. The first step, PI3K, is mediated by a cell-surface receptor called phosphatidylinositol triple kinase. (A kinase is an enzyme that mediates phosphorylation of a biomolecule, a key step in many biological reactions.)

Akt is also known as protein kinase B, and its activity is controlled by a phosphatase-and-tensin homolog called PTEN. (A phosphatase is the opposite of a kinase; it removes a phosphate rather than adding one).

Further along in the pathway is a complex of two kinds of mTOR, one of which controls the synthesis of proteins through ribosomal proteins such as S6K. (Ribosomes are molecular machines that translate mRNA to proteins, and they are themselves partly constructed of proteins). Other functions of the PI3K/Akt/mTOR pathway include control of apoptosis (programmed cell death) and repair of DNA damage. To illustrate the complexity of this system, there can be as many as 10 million ribosomes in a single mammalian cell, and there are approximately a billion cells in a one-gram tumor.

Lipid rafts, pathway activation and phosphorylation waves. A signaling pathway is said to be activated if it is capable of running continuously without external controls. The PI3K-Akt-mTOR pathway is activated by double phosphorylation of Akt with two different kinases, mTORC2 and PDK1. These actions occur in lipid rafts, which are microdomains in the plasma membrane delineated by regions high in cholesterol and sphingolipids. For more details, see Gao et al. (Proceedings of the National Academy of Sciences of the U.S. of America 108, 14509-14514 (2011)).

Compartmentalization into microdomains is essential for activation of Akt by PDK1 and mTORC2 (two phosphorylation events). One effect of membrane localization is an increase in concentration of signaling proteins, which leads to a rapid switch-like response.

Moreover, the inhibitory signaling protein PTEN is localized outside the membrane rafts and cannot interfere with the activation. Gao et al. used genetic engineering to modify the lipids in the raft so that PTEN was no longer excluded; they found that when PTEN could enter the rafts, it abolished the activity of the whole pathway (Gao et al., Proceedings of the National Academy of Sciences of the U.S. of America 108, 14509-14514 (2011))).

Following the double phosphorylation, the activated Akt escapes from the lipid raft with the help of PIP3 and then migrates to ribosomes in the cytoplasm and nucleus. One might expect this migration to be diffusive, but it has been shown that the activated Akt molecules actually propagate as phosphorylation waves (Markevich et al., Molecular Systems Biology 2, 61 (2006)). These waves are created by the feedback paths shown in FIG. 1. Markevich et al. also shows that the positive feedback leads to bistability, with the two states being Akt singly phosphorylated and doubly phosphorylated. The resulting pair of coupled waves then propagates with little attenuation or scattering, greatly enhancing their efficiency in passing their activation on to ribosomes.

It would appear to be straightforward to construct a characteristic functional incorporating all aspects of this pathway. Such a theory would take advantage of the fact that the initiating events—Akt activations—are statistically independent since they take place in isolated lipid rafts, one activation at a time. That means that the whole set of activated Akts is well described as a sample function of a Poisson random process, with a well-known characteristic functional (Barrett and Myers, "Foundations of Image Science," Wiley-Interscience, Hoboken, NJ (2004)).

Example 3—COVID-19 Disease

Introduction. In essence, a virus is a segment of genetic material inside a protein shell. A virus is not a living being, rather a parasite that replicates within a host cell. The particular virus discussed here is an RNA virus called SARS-CoV-2, for "Severe Acute Respiratory Syndrome-CoronaVirus-2". The associated disease, called COVID-19, was discovered in December, 2019, in Wuhan, China.

By early February, 2020, remarkably detailed papers by Chinese scientists had been published (online or in print) in world-renowned scientific journals barely six weeks after the first cases in Wuhan (Wang et al., The Lancet 395, 470-473 (2020); Li et al., The New England Journal of Medicine 382, 1199-1207 (2020); and Wu et al., Nature 579, 265269 (2020)). It was apparent that the new disease was closely related to SARS and MERS, hence also a corona virus. By this same time frame, Chinese scientists had determined and published the full genome of the virus, and the World Health Organization (WHO) had declared a pandemic.

Mechanisms of viral infection. The early Chinese papers established that the probable entry routes by which a novel corona virus could infect a cell were essentially the same as for SARS and MERS. A 2012 review of SARS and MERS (Belouzard et al., Viruses 4, 1011-1033 (2012)), focused on the role of the viral spike protein (S) in mediating cell entry. The process starts with conformational changes of the S protein triggered by receptor binding, pH changes or other stimuli.

For pulmonary infections the relevant receptors are the angiotensin converting enzyme 2 (ACE2) and the angiotensin receptor (AR). Each of these is associated with a common class of drugs for hypertension: ACE inhibitors (ACEI) and AR blockers (ARB). Another molecule that is important to the entry process is transmembrane protease serine 2 or TMPRSS2.

As an aside, some early investigators suggested using ACEIs and ARBs in conjunction with other COVID-19 therapy, but there was always some concern about interfering with normal respiratory function. A few recent clinical trials have shown, however, that there may be some benefit in continuing with hypertension drugs during any therapy on hypertensives.

Returning to mechanisms of coronavirus infection, it is not completely clear what happens after a virus enters a cell at an ACE2 or AR site. Wang et al. ("The role of high cholesterol in age-related COVID19 lethality," Biorxiv (2020)) shows fairly convincingly that entry is facilitated by high levels of cholesterol, which they presume to be stored in lipid rafts in the plasma membrane. These lipid rafts, however, do not have the same physical structure as the ones discussed above in the context of the mTOR pathway. The latter are anchored by transmembrane receptors, and they are delineated by high levels of cholesterol and sphingolipids that serve the important function of keeping the inhibitory protein PTEN out of the raft.

The lipid rafts of interest for COVID19 are not so sharply delineated; they can migrate laterally on the membrane and merge to form larger rafts. On the other hand, they can serve as cholesterol repositories, thereby accounting for the increased susceptivity to COVID 19 for older patients.

Inflammation, cytokine storm. There is considerable discussion on line about how to define disease mortality, but an intuitive practical definition is number of deaths divided by the number of confirmed cases; by this token the mortality of COVID-19 in the US is about 5%. This number is substantially higher for elderly patients or those with comorbidities, and it is much less for children.

For all ages, it appears that a large fraction of the deaths are the result of cytokine storms, or colloquially, the immune system run amok.

A cytokine is a signaling molecule that initiates movement of other molecules. The cytokines known to be relevant to COVID 19 include several interleukins, VEGFA, TNF and MCP1. For many more details, see Nile et al. (Cytokine and Growth Factor Reviews 53, 66-70 (2020)).

Of these cytokines, perhaps the easiest to understand is MCP1 (Monocyte Chemoattractant Protein 1), also known as CCL2. A monocyte is a leukocyte (white blood cell), but a primitive one very early in its development. An inflamed tissue can send out MCPI and receive a cloud of monocytes in return; the monocytes then differentiate into tissue resident macrophages, which can engulf inflamed cells. One way this process can stop is by further differentiation to foam cells, but little is known about the efficiency of this step. If the process does not stop, a cytokine storm ensues.

Accordingly, molecular imaging might be a good tool for early detection of cytokine storms.

Vaccines and therapeutics. Further understanding of the biological effects and mechanisms of potential vaccines and therapeutics for COVID-19 and other viral diseases would greatly improve the development of vaccines and treatments. For example, a readable and informative survey for COVID 19 vaccines or therapeutics is given by J. Timmer ("COVID-19: the biology of an effective therapy," Ars Technica, arstechnica.com/science/2020/03/covid-19-the-biology-of-an-effective-therapy (2020)).

Accordingly, it would be beneficial to be able to image or provide data on the biological processes involved with potential vaccines and therapeutics, such as the interactions between the vaccine or therapeutic, cell surface receptors, the virus, and molecules within the cell.

Role of characteristic functionals. So far characteristic functionals have been treated mainly as tools for estimating stochastic properties of physiological random processes, but they can also play a role in hypothesis testing. Suppose, for example, that K radioactive tracers with different energies are used to study K PRPs. The vector Φ then signifies K separate functions of three spatial dimensions, one for each energy. If K is large, an imaging gamma-ray detector will be needed with excellent energy resolution to acquire K separate SPECT images. It would not suffice to have a narrow photopeak; spurious peaks arising from escape of fluorescent X rays or Compton-scattered photons would also have to be suppressed.

A general method for suppressing these spurious peaks is based on the Maximum-Likelihood Expectation-Maximization (MLEM) algorithm as applied to energy spectra (Eskin et al., "Recovery of spectral information from an imperfect detector using the expectation maximization algorithm," in Proceedings of 1994 IEEE Nuclear Science Symposium, 150-154 (1994)). With this tool and any reasonably good SPECT system, the vector Φ can be used to scan the reconstructed images for missing peaks or unexpected peaks that could represent potential therapeutic targets for that specific patient. This procedure can be viewed as testing the dual hypothesis that all relevant proteins have been included in the mathematical model and none have been missed.

Example 4—Example of Application of Characteristic Functionals to COVID-19

There are many possible applications in COVID-19 virology to which ECT and characteristic functionals could be applied. For each, an important biological or clinical question would have to be defined; a relevant ECT imaging modality and associated tracers chosen, and a data-acquisition strategy designed. The example provided in this section was inspired by the recent discovery of a new mutated strain of COVID-19 that is 5-10 times more infectious than the original strain from Wuhan, yet paradoxically no more lethal.

Figure 2:
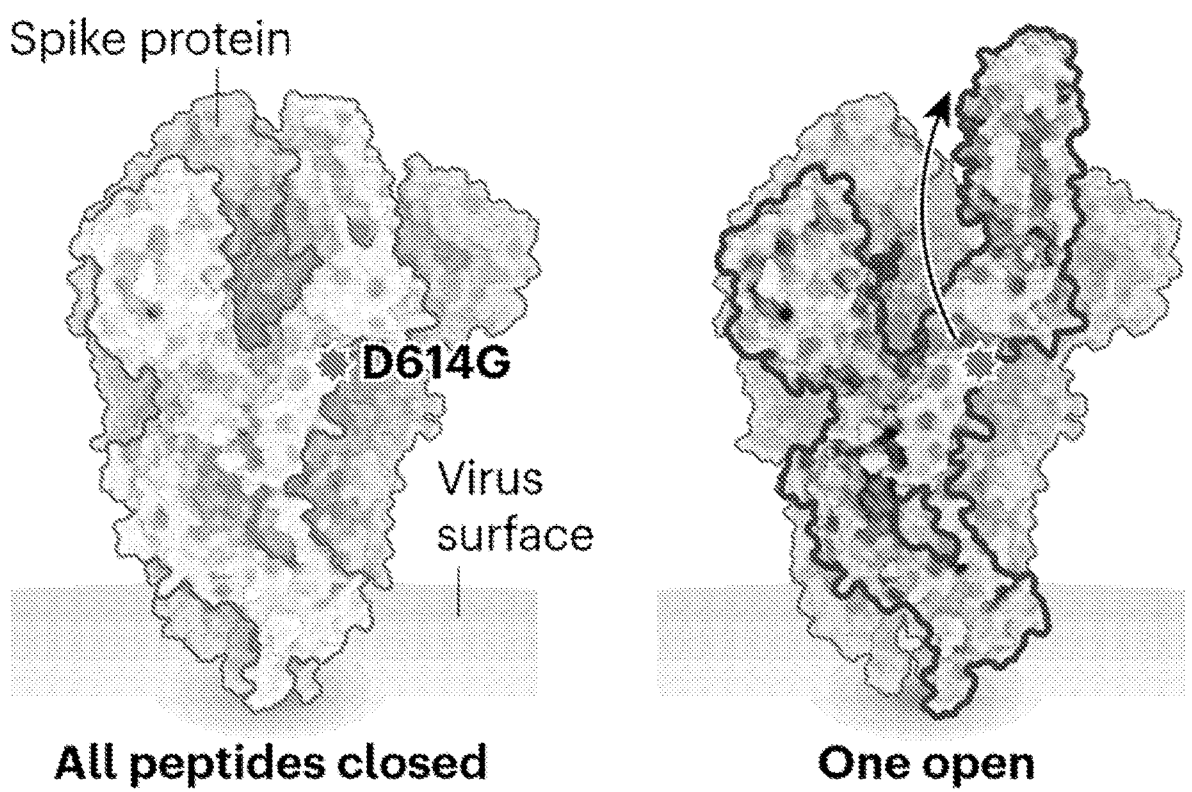
FIG. 2 Spike proteins on COVID-19 bind to receptors on human cells, helping the virus to enter. A spike protein is made up of tree smaller peptides in 'open' or 'closed' orientations; when more are open, it is easier for the protein to bind. The D614G mutation seems to relax connections between peptides (Callaway, E., Nature 585, 174177 (2020)).

In a comprehensive worldwide epidemiological study, Korber et al. (Cell 182, 812-827 (2020)) established the nature of this mutation, which turns out to be a change in a single amino acid at one particular location in the genome of the spike protein. According to Korber (Cell 182, 812-827 (2020)), when the SARS-COV-2 virus emerged in Europe in January 2020, almost 100% of clinical samples in the study coded for aspartic acid (symbol D) in position 614 in the spike protein. By May 2020, the virus had mutated, at least in Europe, so that the same location now coded for glycine (symbol G) in almost 100% of cases. This transition, denoted Spike D614G, results in a 5-10-fold increase in infectivity (see FIG. 2).

To see why this seemingly minor genetic modification causes such a major change in viral function, it is noted that glycine is the only achiral amino acid, which in simple terms means that it can be superimposed on its mirror image by rotations and translations. All other amino acids have complex sidechains that prohibit this superposition; in glycine the sidechain is just a hydrogen atom. Glycine does not exhibit optical activity and it is neither left-handed nor right-handed. In proteins and other large biomolecules, glycine permits sharp turns in the folded chains.

Though the D614G mutation described above accounts for the increased infectivity, it does not explain the apparent absence of increased clinical lethality. For this purpose, mathematical models of viral cell entry are needed akin to those used by Henscheid et al. (PloS One 13 (6), e0199823 (2018)) for oncology. Several models of infection and cell entry have appeared in the literature; each is characterized by a small number of proteins. These proteins can be made visible to a fluorescence imaging system by labeling them with a fluorescent peptide. If a data-acquisition system is used in its standard operating mode, then the various proteins can be depicted in a pseudocolor image.

Figure 3:
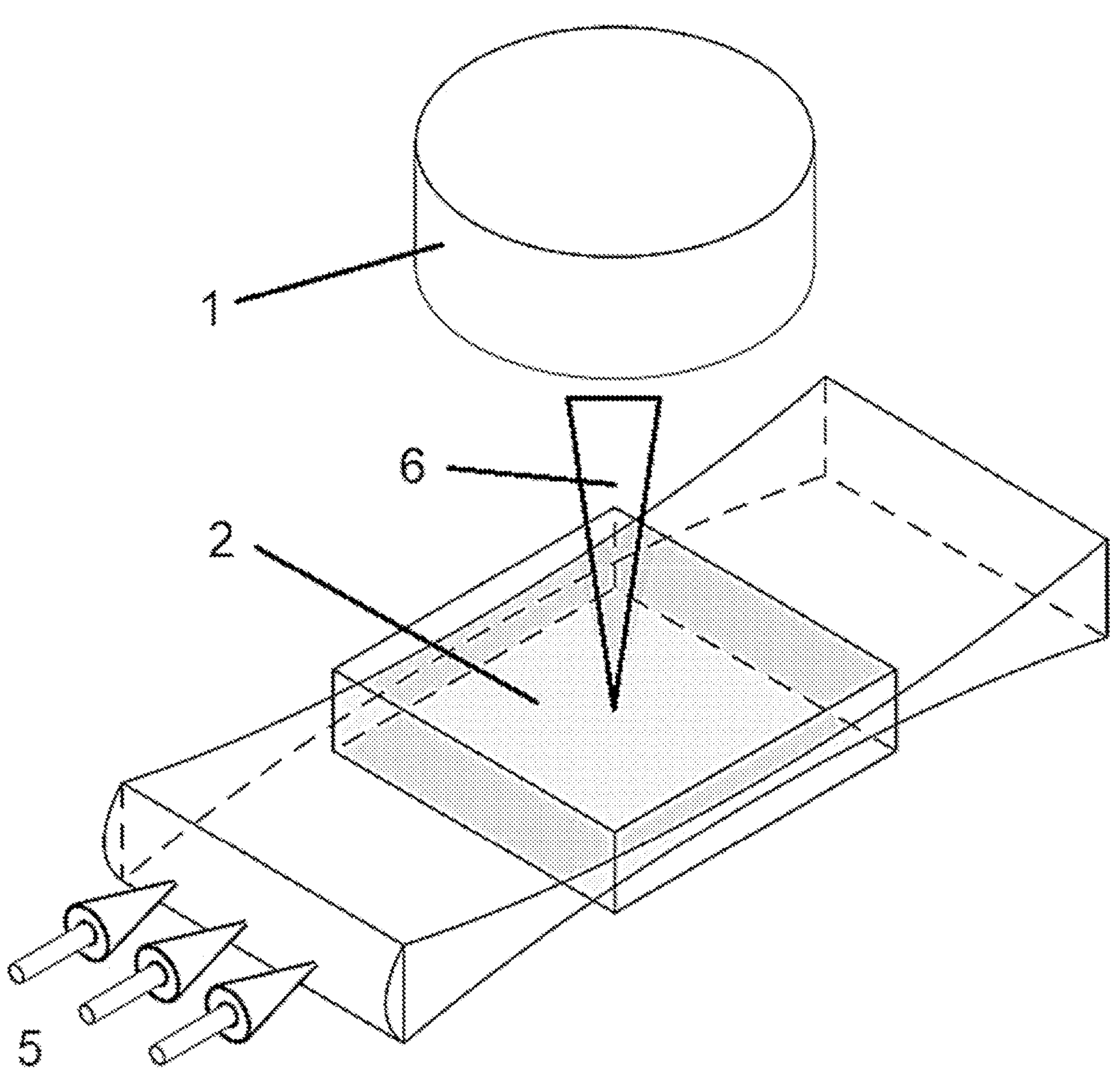
FIG. 3 shows a generic setup of light sheet fluorescence microscopy. A thin plane of light (vertical) is created with a cylindrical lens. The plane of light is used to optically section a piece of transparent tissue (center square). Imaging is done perpendicularly to the direction of illumination.

FIG. 3 shows one example of a suitable data-acquisition system using light sheet fluorescence microscopy, although it should be noted that other imaging systems can be used. A camera unit 1, typically including one or more lenses, is placed above a tissue sample 2. Incoming light 5 is used to illuminate the tissue sample 2 perpendicular to the direction of observation. The resulting emitted fluorescent light 6 is then imaged by the camera unit 1.

No information is obtained, however on the spatial and temporal statistics of the corresponding physiological random processes; in particular, there is no information about how different PRPs interact with each other. These deficiencies can be remedied by using the data from the light-sheet imager to construct characteristic functionals for the relevant PRPs and from there construct a complete multivariate (really multi-PRP) characteristic functional by use of Eq. 5. From there many properties of any proposed cell-entry mechanism can be computed, and the mechanism that is most consistent with the image data can be found.

Figure 4:
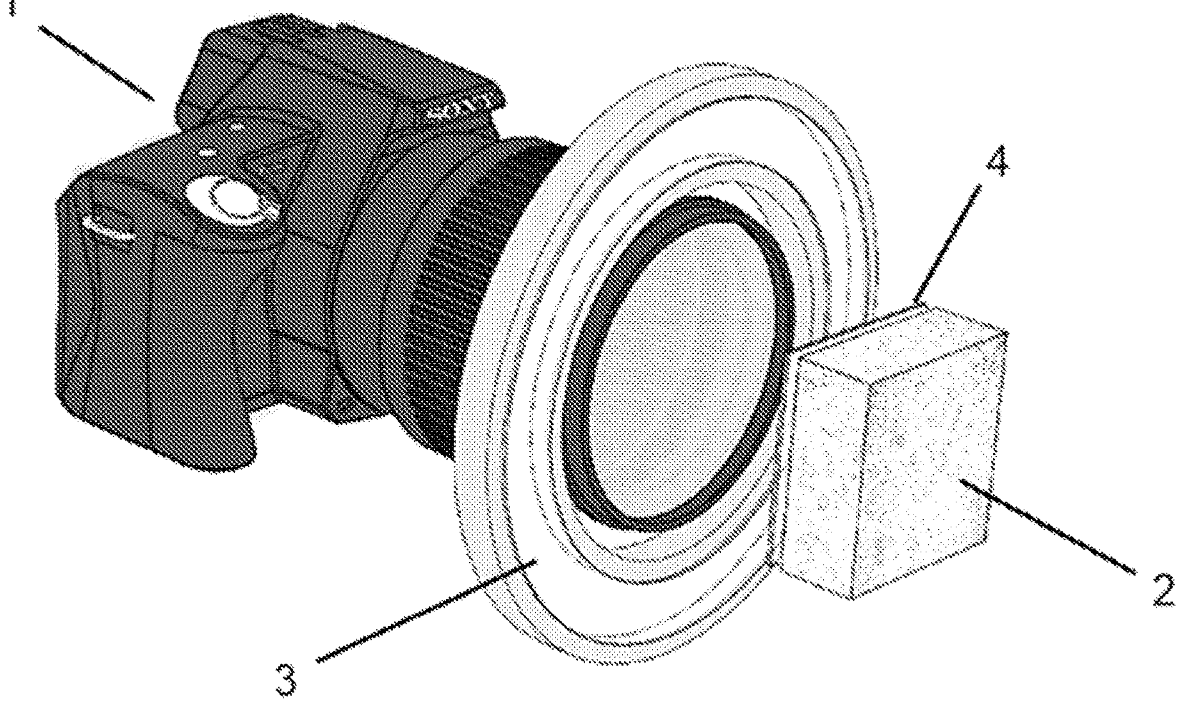
FIG. 4 shows a generic setup of a high-resolution fluorescence imaging system. As the tissue sample is translated axially, different planes within the tissue sample are focused, and the emitted fluorescence light is imaged by the camera's detector. Suitable cameras include Sony mirrorless interchangeable-lens cameras, such as the Sony α 1 camera (50 MP CMOS sensor and up to 30 fps shooting).

Example 5—Using High-Resolution Cameras to Estimate Characteristic Functionals of Intestinal Epithelium Cell Cultures An exemplary setup able to collect fluorescence imaging data with which to estimate parameters of characteristic functionals is also illustrated FIG. 4, although other imaging systems can also be used. In this embedment, a camera 1 is placed in front of a tissue sample 2 containing fluorescent tags. The excitation light is provided by a UV light ring 3 surrounding the lens of the camera 1. Thus, the direction of illumination and observation are along the same axis. A filter 4 is optionally placed in front of the tissue sample 2 to improve the quality of the resulting imaging data.

This setup enables fluorescence imaging of cell cultures for the study of grown dynamics in response to various signals, and also enables validation of characteristic functionals by imaging well-known cell dynamics, a prominent example being those found in intestinal epithelium cell cultures.

The intestinal epithelium is a single-cell layer that covers the inside of the small and large intestine of the gastrointestinal tract. The intestinal epithelium maintains a very large and uniform array of villi (protrusions that develop into the gut lumen to absorb nutrients) and crypts, which occupy the space between villi. Disorganization of the crypt-like regions has been observed to evolve into many intestinal diseases, including inflammatory bowel disease and cancers of the gastrointestinal tract (see Maloy et al., Nature, 474 (7351), 298-306 (2011); Terzić et al., Gastroenterology, 138

(6), 2101-2114.e5 (2010); Schepers and H. Clevers, Cold Spring Harbor perspectives in biology, 4 (4), a007989 (2012); and Radtke and Clevers, Science 307 (5717), 1904-9 (2005)).

Recent research has shown that the renewal of intestinal epithelium cells is affected by two opposite signaling pathways: (1) the WNT signaling pathway, which promotes cellular proliferation, differentiation, apoptosis and migration; and (2) the bone morphogenetic protein (BMP) which promotes terminal differentiation of the intestinal secretory-cell lineage, and has also been shown to inhibits intestinal stem-cell self-renewal by suppressing WNT signaling (see Thorne et al., Developmental Cell, 44 (5), 624-633.e4 (2018); Flanagan et al., Genes, 9 (4), 178 (2018); Blanpain and Fuchs, Science, 344 (6189), 1242281 (2014); Auclair et al., Gastroenterology, 133 (3), 887-96 (2007); and He et al., Nature genetics, 36 (10), 1117-21 (2004).

Starting from an organoid model, it is possible to establish an in vitro culture of the intestinal epithelium that recapitulates the structure and functions of in vivo epithelial cells (Kim et al., Nature reviews. Molecular cell biology, 21 (10), 571-584 (2020); Hofer and Lutolf, Nature reviews. Materials, 1-19 (2021); and Thorne et al., Developmental Cell, 44 (5), 624-633.e4 (2018)). This includes various morphogenesis characteristics, including crypt-villus spatial organization, cell-type composition and renewal dynamics.

The way in which WNT and BMP signaling affects morphogenesis was revealed in Thorne et al. by modulating various sources of WNT and BMP signaling. For example, epithelial-intrinsic BMP signaling was inhibited with LDN-193189 treatment, resulting in increased proliferation as well as disorganization of the crypt-like regions (Chen et al., Nature chemical biology, 5 (2), 100-7 (2009); and Cuny et al., Bioorganic & medicinal chemistry letters, 18 (15), 4388-92 (2008)). This outcome is assessed in Thorne et al. and virtually everywhere else quite elementarily by computing distances between neighboring pairs of proliferative cells before and after treatment.

The ability to fine tune renewal dynamics of various structures and cell types in the intestinal epithelium by controlling WNT or BMP (or both) allows one to create in vitro cultures for which the ground truth is known. Imaging of these cultures can be done with various fluorescence dyes and to study different properties (e.g., antigen Ki-67 to mark cell proliferation). It is possible to validate the imaging system of FIG. 4 and benchmark its performance in terms of its ability to produce data that are quantitatively in agreement with what the intestinal epithelium cultures are supposed to look like in response to WNT- and/or BMP-induced morphogenesis. Similarity measures (e.g., Bhattacharyya distance as described in Bulletin of the Calcutta Mathematical Society, 35, 99-109 (1943)) can be used to quantify the degree of deviation between our estimates and those found in Thorne et al. and elsewhere in the literature.

Example 6—Summary

All disease processes are enormously complicated, involving many physiological processes and both patient-to-patient and cell-to-cell variability. These experiments demonstrate that characteristic functionals are a systematic tool for understanding interactions among physiological random processes, even those involving external therapeutic agents. Moreover, physiological random processes can virtually always be observed directly with in vivo molecular imaging. These observations can then be connected to models describing the interactions among random processes, thus potentially verifying the theories or leading to refinements of them. Detailed validation is needed, but this formalism holds great promise as a tool for biomedical research and clinical medicine.

An immediate challenge in this field is to develop efficient methods for estimating patient-specific and disease-specific characteristic functionals for multiple physiological random processes. An important extension of the above experiments is to set confidence intervals on estimated variances or other uncertainty measures, taking into account both measurement errors and model inaccuracy. In some embodiments, the ultimate performance metric could be a Therapy Operating Characteristic (TOC) curve (Barret et al., Journal of Medical Imaging 3, 023502 (2016)).

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising," particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A method for modeling a biological process in a cell or tissue comprising the steps of:
a) performing multiple imaging scans of one or more cells or tissues containing a selected biological process of interest;
b) generating image data of one or more physical characteristics related to the selected biological process;
c) calculating or estimating a characteristic functional from said image data for the one or more physical characteristics; and
d) analyzing the characteristic functional to extract information from the biological process, wherein the physical characteristics related to the selected biological process comprise:
i) presence of one or more molecules or structures in the cell or tissue;
ii) quantity of one or more molecules or structures in the cell or tissue;
iii) location of one or more molecules or structures within the cell or tissue;
iv) binding of one or more molecules to a second molecule;
v) conformational structure of one or more molecules;
vi) size of one or more structures; or
vii) combinations thereof, wherein the biological process is a disease related to mutations of mTOR signaling pathways or intestinal epithelium growth.

2. The method of claim 1, wherein the biological process is related to a disease and the multiple scans are used to model progression of the disease.

3. The method of claim 1, wherein the biological process is related to progression of a viral infection.

4. The method of claim 1, wherein the biological process is related to progression of COVID19 or infection of cells by a severe acute respiratory syndrome coronavirus.

5. The method of claim 1, wherein the modeling data generated from the characteristic functional indicates an increase or decrease in the amount of the one or more molecules or structures, interactions of the one or more molecules or structures with other molecules or structures, or conformational changes of the molecule or structure of interest over time or in response to exposure to a chemical, biomolecule or drug.

6. The method of claim 1 comprising labeling one or more proteins within the one or more cells or tissues with a fluorescent peptide prior to performing the multiple imaging scans.

7. The method of claim 1, wherein the image scans are obtained using a camera or imaging device able to transmit fluorescent excitation radiation to the one or more cells or tissues and measure resulting light emitted by a fluorescently labeled molecule.

8. The method of claim 1, wherein the image scans are obtained using positron emission tomography (PET), single-photon emission computed tomography (SPECT), or light sheet microscopy.

9. The method of claim 1 comprising performing multiple imaging scans of cells or tissues from different patients.

10. The method of claim 1 comprising performing multiple imaging scans of the same cell or tissue over a period of time and analyzing a change in the one or more physical characteristics over time.

11. The method of claim 1, wherein one or more imaging scans are performed prior to administering a treatment to the cell or tissue, and one or more imaging scans are performed after administering the treatment to the cell or tissue.

12. A method for modeling a biological process in a cell or tissue comprising the steps of:
a) labeling one or more proteins within one or more cells or tissues containing a selected biological process of interest with a fluorescent peptide;
b) performing multiple imaging scans of the one or more cells or tissues containing the selected biological process, wherein the one or more proteins are labelled with the fluorescent peptide prior to performing the multiple imaging scans;
c) generating image data of one or more physical characteristics related to the selected biological process;
d) calculating or estimating a characteristic functional from said image data for the one or more physical characteristics; and
e) analyzing the characteristic functional to extract information from the selected biological process, wherein the physical characteristics related to the selected biological process comprise:
i) presence of one or more molecules or structures in the cell or tissue;
ii) quantity of one or more molecules or structures in the cell or tissue;
iii) location of one or more molecules or structures within the cell or tissue;
iv) binding of one or more molecules to a second molecule;
v) conformational structure of one or more molecules;
vi) size of one or more structures; or
vii) combinations thereof.

13. The method of claim 12, wherein the selected biological process is related to a disease and the multiple scans are used to model progression of the disease.

14. The method of claim 12, wherein the selected biological process is related to progression of a viral infection.

15. The method of claim 12, wherein the selected biological process is related to progression of COVID19 or infection of cells by a severe acute respiratory syndrome coronavirus.

16. The method of claim 12, wherein the modeling data generated from the characteristic functional indicates an increase or decrease in the amount of the one or more molecules or structures, interactions of the one or more molecules or structures with other molecules or structures, or conformational changes of the molecule or structure of interest over time or in response to exposure to a chemical, biomolecule or drug.

17. The method of claim 12, wherein the image scans are obtained using a camera or imaging device able to transmit fluorescent excitation radiation to the one or more cells or tissues and measure resulting light emitted by a fluorescently labeled molecule.

18. The method of claim 12, wherein the image scans are obtained using positron emission tomography (PET), single-photon emission computed tomography (SPECT), or light sheet microscopy.

19. The method of claim 12 comprising performing multiple imaging scans of cells or tissues from different patients.

20. The method of claim 12 comprising performing multiple imaging scans of the same cell or tissue over a period of time and analyzing a change in the one or more physical characteristics over time.

21. The method of claim 12, wherein one or more imaging scans are performed prior to administering a treatment to the cell or tissue, and one or more imaging scans are performed after administering the treatment to the cell or tissue.

* * * * *